United States Patent [19]

Humphrey et al.

[11] Patent Number: 5,470,976
[45] Date of Patent: Nov. 28, 1995

[54] PROCESS FOR THE STEREOSELECTIVE REDUCTION OF STEROID ENELACTAMS

[75] Inventors: Guy R. Humphrey, Belle Mead; Ross A. Miller, Fanwood, both of N.J.

[73] Assignee: Merck & Co., Inc., Rahway, N.J.

[21] Appl. No.: 301,949

[22] Filed: Sep. 7, 1994

[51] Int. Cl.$^6$ .................................................. C07D 221/18
[52] U.S. Cl. ............................................................. 546/77
[58] Field of Search ......................... 546/77, 78; 514/284

[56] References Cited

U.S. PATENT DOCUMENTS 5,237,064  8/1973  Bakshi et al. ............................... 546/77

FOREIGN PATENT DOCUMENTS 1465544  1/1967  France ...................................... 546/77
3612632  10/1987  Germany .

OTHER PUBLICATIONS

Sakura et al., Tetrahedron 46(3); 761–774 (1990).
Templeton et al., J. Chem. Soc. Perk T 1(6), 1361–1368 (1987).
Larpent et al., Tetrahedron Lett, 28(22), p. 2507 (1987).
Kharchenko et al. Zh. Org. Khim+ 23(3), 576–581 (1987) in Russian.
Abad et al. Tetrahedron Lett. 2728) 3289–3292 (1986).
Stork et al. J. Amer. Chem. Soc. 105, p. 1072 (1983).
Suggs et al. Tetrahedron Lett. p. 303 (1981).
Kollar et al. J. Mol. Catal. 47(1) 33–9 (1988).

*Primary Examiner*—Donald G. Daus
*Attorney, Agent, or Firm*—Catherine D. Fitch; Carol S. Quagliato

[57] ABSTRACT

The novel process of this invention involves the reduction of certain Δ-5 steroidal alkenes to selectively produce either the 5α or 5β reduction products. Particularly, this invention involves reduction of Δ-5 steroidal alkenes using a rhodium based catalyst in the presence of hydrogen to selectively yield 5α steroids or alternatively reduction of Δ-5 steroidal alkenes in an ionizing medium with a trialkylsilane to selectively yield 5β steroids.

18 Claims, No Drawings

PROCESS FOR THE STEREOSELECTIVE REDUCTION OF STEROID ENELACTAMS

FIELD OF THE INVENTION

The present invention is concerned with a novel process for the stereoselective reduction of enelactams. The process is particularly useful for the reduction of Δ-5 steroidal enelactams.

BACKGROUND OF THE INVENTION

The principal mediator of androgenic activity in some target organs, e.g., the prostate, is 5α-dihydrotestosterone ("DHT"), formed locally in the target organ by the action of 5α-reductase, which converts testosterone to DHT. Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Inhibitors of 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

The reduction of Δ-5 steroidal alkenes to the corresponding saturated compounds is an important step in the synthesis of steroid end-products useful as 5α-reductase inhibitors.

Platinum, palladium/carbon, and noble metals such as nickel have been previously used as catalysts in the reduction of Δ-5 steroidal enelactams to prefererentially yield the corresponding 5α-steroid. The degree of selectivity varies according to the particular steroidal enelactam being reduced. The best selectivity achieved using these catalysts to reduce 4,7β-dimethyl-4-aza-cholest-5-ene-3-one and its 4-NH analog is about 100:1 of α:β product. Because the resulting α/β mixture can be purified only with great difficulty, it was desirable to develop a reduction process exhibiting greater selectivity for the α-reduction product. Furthermore, none of the previously described reductions, catalytic or otherwise, offered any way to selectively direct hydrogenation to obtain the 5β reduction products which are also useful as 5α-reductase inhibitors.

The instant invention provides an improved method for stereoselective reduction of certain Δ-5 steroidal enelactams. In the case of 4,7β-dimethyl-4-aza-cholest-5-ene-3-one, process parameters can be adjusted to preferentially yield the α-reduction product over the β-reduction product in a ratio of about 500:1. The α-reduction product of 7β-methyl-4-aza-cholest-5-ene-3-one is selectively formed over the β-reduction product in a ratio of about 264:1. Alternatively, the process parameters can be varied to selectively yield the β-reduction product of 4,7β-dimethyl-4-aza-cholest-5-ene-3-one and its 4-NH analog over the α-reduction products by ratios of about 60:1 and 90:1 respectively.

SUMMARY OF THE INVENTION

The novel process of this invention involves the reduction of certain Δ-5 steroidal alkenes to selectively produce either the 5α or 5β reduction products. Particularly, this invention involves reduction of Δ-5 steroidal alkenes using a rhodium based catalyst in the presence of hydrogen to selectively yield 5α steroids or alternatively reduction of Δ-5 steroidal alkenes in an ionizing medium with a trialkylsilane to selectively yield 5β steroids. This novel process can be exemplified in the following embodiment.

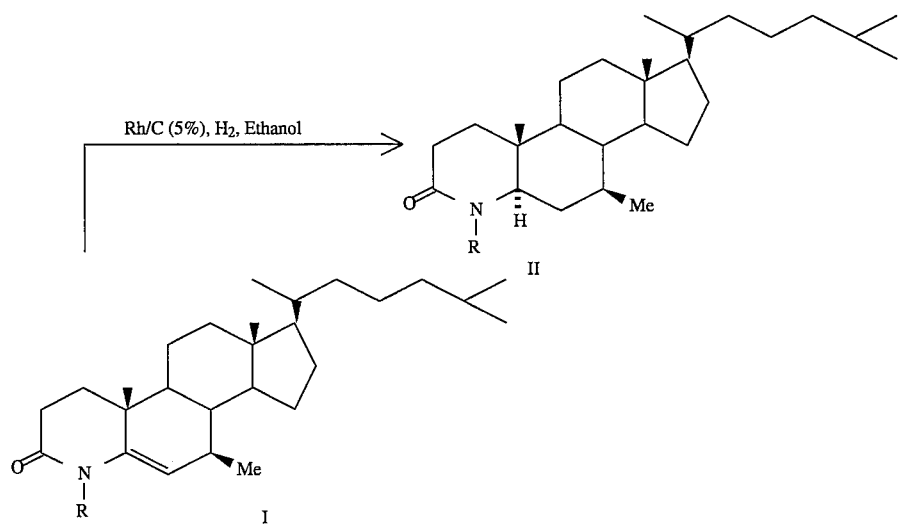

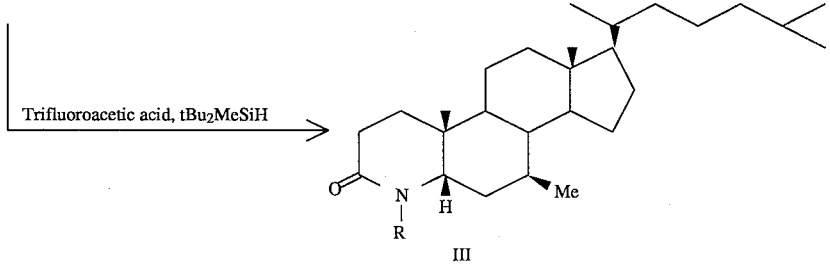

wherein R is selected from H and $C_1$–$C_5$ alkyl.

The α-reduction product corresponding to Formula II and the β-reduction product corresponding to Formula III are useful as 5α-reductase inhibitors or as intermediates in the preparation of 5α-reductase inhibitors. 5α-eductase inhibitors are useful in the treatment of hyperandrogenic disorders such as benign prostatic hyperplasia, acne vulgaris, seborrhea, female hirsutism, androgenic alopecia, male pattern baldness, and the prevention and treatment of prostatic carcinoma.

DETAILED DESCRIPTION OF THE INVENTION

The novel process of this invention allows for greater stereoselective control than previously possible over the reduction of Δ-5 steroid enelactams.

Reduction of Δ-5 steroidal enelactams to 5α-steroidal lactams using platinum, palladium/carbon, and noble metals such as nickel catalysts is described in U.S. Pat. No. 5,237,064, issued Aug. 17, 1993. The degree of selectivity varies according to the particular steroidal enelactam being reduced. The best selectivity achieved using these catalysts to reduce 4,7β-dimethyl-4-aza-cholest- 5-ene-3-one and its 4-NH analog is about 100:1 of α:β product. Because the resulting α/β mixture can be purified only with great difficulty, it was desirable to develop a reduction process exhibiting greater selectivity for the a-reduction product. The process of the present invention leads to stereoselective α/β ratio at least twice that of the prior reductions.

Acidic hydride reductions of various fused ring alkenes have been reported in which one stereoisomer product predominates depending on the nature of the alkene substrate. Bulky silanes have been used to provide high selectivity in the reduction of a non heteroatom stabilized alkene (octahydronaphthalene to decahydronaphthalene), with the β product predominating. See Doyle, M. P., McOsker, C. C., J. Org. Chem., 43(4), 693–696 (1978). Acidic hydride reduction of ene-lactams, however, has been reported to reduce ene-lactam with the 5α-product predominating. See, e.g., Rasmusson, et al., J. Med. Chem., 27, 1690 (1984); Rasmusson, et al., J. Med. Chem., 29, 2298 (1986); Jones, et al., J. Med. Chem., 36,421 (1993); Cannon, et al., Synthesis, 494 (1986); and Murahashi, et al., J. Org. Chem., 2521 (1992). The process of the present invention offers a way to selectively obtain the 5β-reduction products of Δ-5 steroid enelactams by exploiting the surprising discovery that, contrary to published reports, ionic reductions of enelactams favor β face selectivity.

In one embodiment of this invention, a Δ-5 steroidal enelactam is dissolved in solvent and treated with $H_2$ in the presence of a rhodium-based catalyst selected from Rh/Al$_2$O$_3$ (5%) or Rh/C (5%) to preferentially obtain the α-reduction product.

In exemplifications of this invention where Rh/C (5%) is employed as the catalyst, the solvent used is a $C_{1-6}$ alcohol, such as methanol, ethanol, n-propanol, isopropanol, etc. In particular, the preferred solvent in the Rh/C catalyzed system is ethanol. When using Rh/Al$_2$O$_3$ (5%) as the catalyst, the solvent is a $C_{1-4}$ alkanoic acid, such as formic, acetic, propionic, or butyric acid. In particular, the preferred solvent in the Rh/Al$_2$O$_3$ catalyzed system is acetic acid.

Those skilled in the art are familiar with the use of catalytic amounts of reaction catalysts and will appreciate that the amount of catalyst that can be used may vary with the scale of the reaction. Generally, the amount of rhodium based catalyst used in the process of the present invention is adjusted so that the weight of rhodium present in the reaction mixture represents between 5–100% and preferably between 10–20% of the weight of the Δ-5 steroid alkene starting material. In particular, a weight of rhodium corresponding to about 20% of the Δ-5 steroid alkene starting material weight is preferred.

The catalytic reduction is preferably run at a $H_2$ pressure of 40 psi, but pressure may be increased to as much as 250 psi in order to reduce the reaction time.

The rhodium catalyzed reduction can be run between about 20°–30° C. and may be conveniently run at room temperatures within this range. Temperatures above this range will adversely affect the selectivity of reduction and it is preferable to maintain the reaction at the lower temperatures within this range.

A second embodiment of the present invention involves refluxing a Δ-5 steroidal enelactam in an ionizing medium such as trifluoroacetic acid with a trialkylsilane to preferentially yield the 5β-azasteroid product. Trialkylsilanes useable in the process of the present invention have the formula $(R^2)_3SiH$ in which each alkyl group represented by $R^2$ may be independently selected from $C_{1-6}$ alkyl and phenyl. In particular, trifluoroacetic acid is the preferred ionizing medium with di-t-butylmethylsilane and tri-t-butylsilane being the preferred trialkylsilanes useable in this embodiment of the invention.

The process of the present invention is useful for the stereoselective reduction of Δ-5 steroidal enelactams of formula I below, wherein R is selected from H and $C_1$–$C_5$ alkyl and $R^1$ is $C_{1-10}$ alkyl.

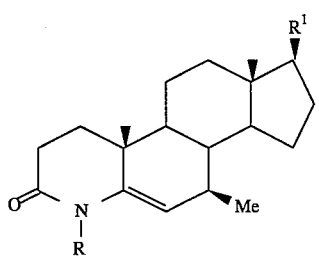

Compounds of formula I are useful for making 7β-methyl substituted 4-azasteroid compounds, and particularly those which are inhibitors of 5α-reductase. Examples of such compounds include but are not limited to those disclosed in U.S. Pat. Nos. 4,377,584 and 4,760,071; WO 93/23419; and WO 93/23420. More particularly, compounds that can be made from an intermediate of formula I in which $R^1$ is 6-methylhept-2-yl include those of general Formula II:

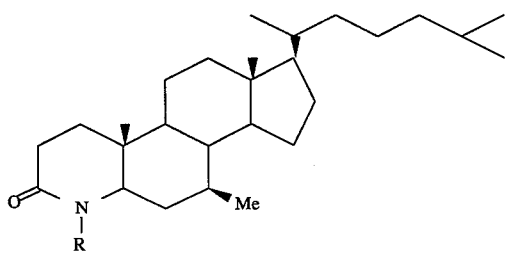

Synthesis of enelactams of formula I is described in U.S. Pat. No. 5,237,064. An exemplary synthetic scheme showing how to make enelactams of formula I and their subsequent reduction to compounds of formula II is as follows:

REACTION SCHEME I

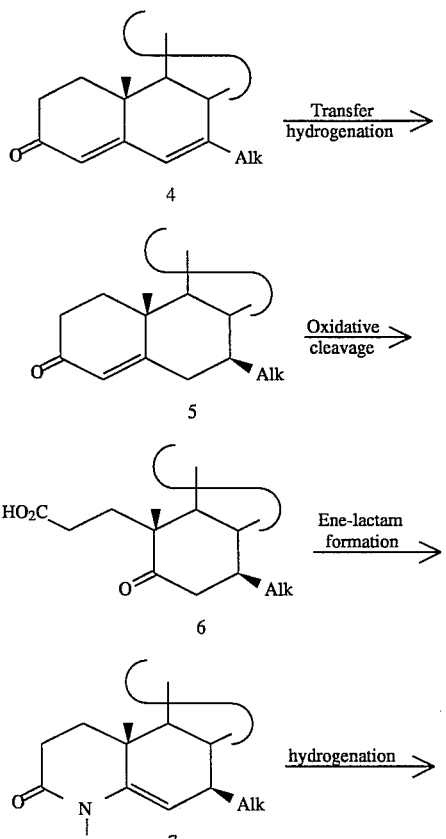

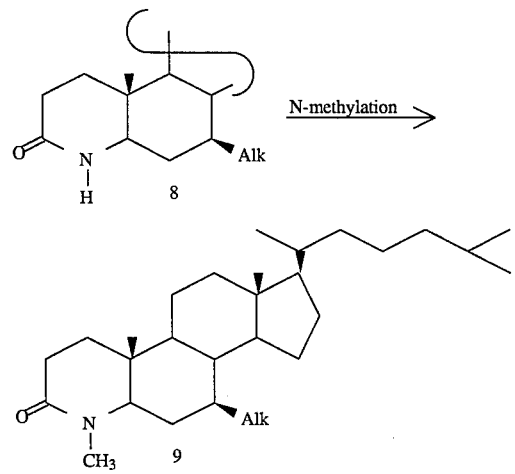

The starting materials for the process generally are the 3-acetoxy-androst-5-enes which are known and available in the art.

As shown in the above Reaction Scheme, the "Alk" substituent can be introduced onto the B ring of the 4-aza steroid generally by the application of an organometallic carbonyl addition reaction, e.g., the Grignard reaction in which the 7-carbonyl group can be reacted with the Grignard reagent containing "Alk" as the R radical in RMgX. The Grignard reaction conditions are conventional and include the use of, e.g., methyl, allyl or cycloalkyl magnesium chloride, ethyl magnesium bromide, cyclopropyl magnesium bromide, and the like. Preferably, the Grignard reagent is used with CeCl₃. Usable dry solvents include, e.g., tetrahydrofuran (THF), diethyl ether, dimethoxyethane, and di-n-butyl ether. The reaction is conducted under dry conditions generally in the temperature range of 0° C. to 40° C. Generally, the reaction requires about 6 to 24 hours for completion. Other organometallic carbonyl addition reactions can be used in this step, such as those utilizing lithium and zinc organometallic reagents which are known in the art.

The adduct 3 is then oxidized with, e.g., aluminum isopropoxide and cyclohexanone (Oppenauer oxidation conditions) in, e.g., refluxing toluene solvent to produce the 7-alkyl-4,6-dien-3-one 4. Other reagents which can be used are, e.g., aluminum ethoxide or aluminum t-butoxide. Other solvents which can be used include, e.g., methylethylketone (MEK) and xylene. The temperature is generally in the range of about 60° to 120° C., and the reaction is carried out under anhydrous conditions and generally requires about 2 to 24 hours for completion.

The dien-3-one 4 is next converted to the 4-ene 5 by treatment with Pd on carbon, DBU (1,8-diazabicyclo[5.4.0] undecene- 7, and cyclohexene in a solvent such as ethanol.

The A Ring is next cleaved by treatment with, e.g., potassium permanganate, sodium periodate in, e.g., t-butylalcohol at 80° C. to produce the corresponding seco-acid 6. Other oxidation reagents which can be used include ruthenium tetraoxide and ozone. Other solvents which can be used are: $CH_3CN$, $CCl_4$, methanol (MeOH) and $CH_2Cl_2$. The reaction generally requires about 2 to 4 hours to proceed to completion.

The seco-acid in a $C_{2-4}$ alkanoic acid such as acetic acid (HOAc) is treated with ammonium acetate at about 15°–30° C. followed by warming to reflux for about 2 to 4 hours. After cooling to about 50°–70° C., water is added and the mixture seeded to cause crystallization of the ene-lactam 7.

Hydrogenation of the ene-lactam to selectively obtain the 5α or 5β-reduction product is accomplished described above and in the examples that follow.

If an N-alkyl compound of formula II is desired, lactam 8 may be N-alkylated as illustrated in Example 2. Alternatively, an N-alkylated enelactam of formula I prepared according to the methods outlined in U.S. Pat. No. 5,237,064, may be directly reduced by the process of this invention as illustrated in Example 3.

Both the 4-N-alkyl and the 4-NH enelactams are unstable in air and the solvent should be degassed prior to dissolving the enelactam and subsequent reduction. In the case of the 4-NH enelactam, an amount of BHT (butylated hydroxy toluene) corresponding to 0.2% of the starting material should also be added to the solvent before dissolving the enelactam.

Representative experimental procedures utilizing the novel process are detailed below. These procedures are exemplary only and should not be construed as being limitations on the novel process of this invention.

EXAMPLE 1

Preparation of 7β-methyl-4-aza-5α-cholestan-3-one

Step 1:

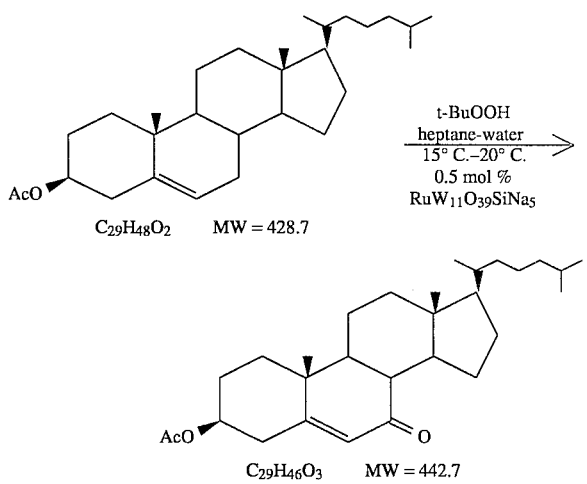

| Materials | Amt | Mole | MW |
|---|---|---|---|
| Cholesteryl acetate (95% Aldrich) | 78.1 gm | 0.173 | 428.7 |
| t-BuOOH (70 wt %, Aldrich) | 189 gm | 1.46 | 90.12 |
| Na₂WO₄-2H₂O | 3.3 gm | 0.010 | 329.9 |
| RuCl₃-xH₂O | 0.24 gm | 0.00116 | 207.43 |
| Sodium metasilicate (Na₂SiO₃) | 0.315 gm | 0.00258 | 122.06 |
| Sulfuric acid (d = 1.84 g/ml, 18 M) | 0.45 ml | 0.0081 | 98.08 |
| Sodium sulfite (Na₂SO₃) | 39 gm | 0.309 | 126.04 |
| heptane | 300 mL | | |
| MEK (methyl ethyl ketone) | 550 mL | | |
| water | 460 mL | | |

In a 2000 mL 3-necked flask was added sodium tungstate dihydrate (3.3 gm), sodium metasilicate (0.315 gm) and 70 mL water and stirred until homogeneous. The solution was neutralized (pH=6– 7) with concentrated sulfuric acid (0.45 mL). A 4° C. exotherm was noted for the addition of acid. Ruthenium trichloride hydrate (240 mg) was added and the mixture stirred for 10 min. Cholesteryl acetate (78.1 gm) and heptane (300 mL) were added to the catalyst mixture. The stirring rate was 225–275 rpm with an overhead paddle stirrer.

70% t-BuOOH (189 gm) was added over 5–10 min. An internal temperature of 15°–20° C. was maintained by cooling with a water bath. The temperature of the batch began to rise slowly after an induction period of 5–15 min. The reaction was stirred until less than 1.5 wt % of s.m. (starting material) and less than 2% of the 7-hydroxy cholesteryl acetate intermediate remained, about 20–24 hrs.

The reaction was monitored with a YMC basic column, 90:10 acetonitrile:water, flow rate=1.5 mL/min, UV detection at 200 nm. Retention times: $t_R$ cholesteryl acetate=17.0 min, $t_R$ 7-keto cholesteryl acetate=7.8 min, $t_R$ enedione 4.5 min, $t_R$ 7 -hydroperoxides, 7-ols intermediates=6.8, 6.9, 7.0, 8.2 min. Later eluting impurities at 18 and 19 min are the 7-t-BuOO-cholesteryl acetates.

To the reaction mixture was added 550 mL MEK, 390 mL water, and 39 gms sodium sulfite. The mixture was heated to 70° C. until the enedione impurity was gone, about 3 hrs. The reaction mixture cooled, then was transferred to a separatory funnel and the aqueous layer cut and then the organic layer washed with 100 mL 1% brine. The MEK and t-BuOH were then removed by an azeotropic distillation with heptane (800 mL heptane added after an initial concentration to 300 mL) until less than 0.7% combined MEK and tBuOH remained as assayed by GC (gas chromatography).

The heptane was checked for MEK and tBuOH levels by GC using an HP-5 column at 35° C. with a 0.5 mL flow rate. $t_R$ MEK=4.9 min, $t_R$ tBuOH=5.3 min, $t_R$ heptane=7.7 min. The volume was adjusted to 350 mL, cooled to −5° C. and filtered, washing twice with 150 mL 0° C. heptane. After drying, the product was obtained as an off-white solid. Melting point (m.p.): 155°–157° C.NMR ($^1$H, 300 MHz, CDCl$_3$): 5.70 (s, 1H), 4.7 (m, 1H), 2.5–0.8 (m, 43H), 0.6 (s, 3H).

Step 2:

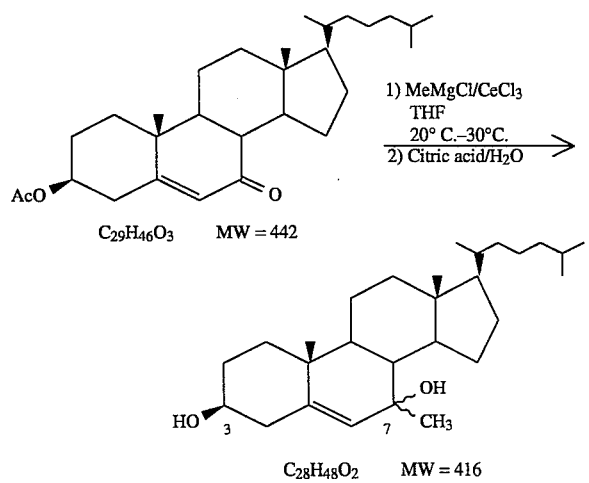

| Materials | Amt | Mole | MW |
|---|---|---|---|
| 7-keto-cholesteryl acetate (95% pure) | 60 gm (as is) | 0.13 | 442 |
| Methyl magnesium chloride (3.0 M) | 160 ml | 0.48 | |
| CeCl$_3$ (anhydrous) | 16.6 gm | 0.068 | 245 |
| THF KF = 50 µg/ml) | 300 ml | | |
| Citric acid | 115 gm | 0.60 | 192 |
| water | 500 ml | | |
| toluene | 600 ml | | |
| sat'd NaHCO$_3$ | 240 mL | | |

Anhydrous cerium chloride (16.6 gm) was stirred as a slurry in THF (150 ml) at 20° C. under N$_2$ for 2h. After two hours a sample of the slurry was removed and showed fine needles under a microscope. To the slurry was added the Grignard reagent (160 ml) and the resulting light purple mixture was aged for 30 minutes.

To the cooled mixture (20° C.) was added the ketone (60 gm at 95% purity, 57 gm by assay) in THF (150 ml) over 50 minutes while allowing the mixture to exotherm to 30° C. Addition of the ketone to the Grignard reagent was exothermic, the exotherm was controlled by the rate of addition. The ketone solution in THF should be warmed to 30° C. to ensure complete dissolution, prior to adding it to the Grignard reagent.

The reaction progress was monitored by HPLC (high pressure liquid chromatography). A 0.5 ml sample was added to 10 ml of 0.1N HOAc and then diluted to 50 ml with CH$_3$CN. HPLC conditions [Zorbax® phenyl column, CH$_3$CN, water, phosphoric acid; 75:25:0.1 gradient elution to 90:10:0.1 at 18 minutes, flow=1.5 ml/min, UV detection at 200 nm]. Retention times, 3,7-diol $t_R$=5.6 and 5.9 min, starting ketone $t_R$=10.9 min, intermediate 7-OH, 3-OAc $t_R$=9.8 and 10.8 min.).

Once complete, the reaction was quenched by adding it to a 0° C. mixture of citric acid solution (115 gm in 300 mL of water) and toluene (300 mL). The quench was exothermic. (NOTE: The rate of addition should be carefully controlled to maintain an internal temperature below 10° C.)

The two phase mixture was stirred for 30 minutes and allowed to stand for 10–15 minutes for an adequate phase separation. The pH of the aqueous layer was ca. 2. The organic phase was separated, washed with water (200 mL, pH=3 after washing) and saturated NaHCO$_3$ solution (240 mL, pH=8 after washing). This afforded 750 ml of an organic layer which contained 66 mg/ml of diol.

The batch was concentrated to 300 ml in vacuo (100–200 mm), diluted to 600 ml with toluene and re-concentrated to 360 ml. The solvent switch to toluene was considered complete when the G.C. area % of THF was <2% of the toluene area %. (NOTE: The first 200 ml of the distillation has a tendency to foam at low pressures. Once this phase is complete, the vacuum should be brought down to 100 mm. The distillation temperature slowly rises from 20° C. to ca. 45° C. as the solvent switch to toluene nears completion.)

Samples of the distillate were assayed for residual THF using G.C. A sample of ca. 0.1 ml was diluted to 1 ml with methanol. G.C. conditions: [HP-5 column (25M, 0.32 µm ID) using a heated block injector, 35° C. isothermal, flow= 0.5 ml/min], MeOH $t_R$=5.5 min, THF $t_R$=6.2 min, toluene $t_R$=10.1 min. The final assay was performed using a sample from the batch.

The organic layer contained 134.4 mg/ml of diols. (NOTE: The KF of the batch should be below 100 µg/ml before proceeding with the next step.)

Step 3:

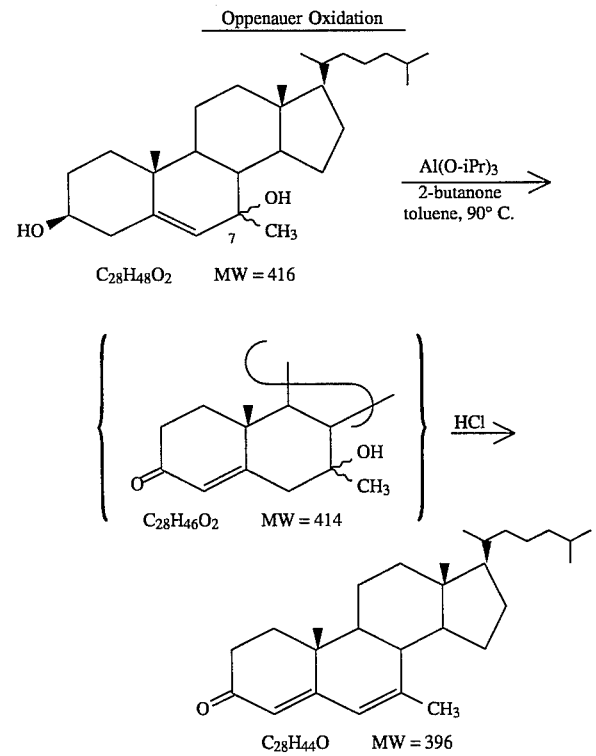

| Materials | Amt | MMole | MW |
|---|---|---|---|
| 7-methyl-7-hydroxy-cholesterol | 30.2 g | 72.6 | 416 |

-continued

| | | | |
|---|---|---|---|
| 2-butanone (d = 0805, KF = 480 μg/ml) | 126 mL | 1404 | 72.11 |
| Aluminum isopropoxide | 18.9 g | 93 | 204.25 |
| 3N HCl | 120 ml | | |
| 5% NaCl solution | 120 ml | | |
| Conc. HCl | 3.5 ml | 42 | |
| D.I. water | 60 ml | | |
| Saturated NaHCO$_3$ | 60 ml | | |

To the toluene solution of the diol (256 mL, 118 mg/mL) was added 2-butanone (126 mL) and aluminum isopropoxide (18.9 g). The solution was heated to reflux (92° C.) under nitrogen. The reaction progress was monitored by HPLC.

The batch was assayed for 2-butanone content by G.C. prior to adding the aluminum isopropoxide. A sample of ca. 0.1 ml was diluted to 1 ml with MeOH. G.C. conditions [HP-5 column (25 m, 0.32 gm ID) using a heated block injector at 250° C., column temp at 35° C. isothermal, flow=0.5 ml/min] 2-butanone $t_R$=6.1 min, MeOH $t_R$=5.5 min, toluene $t_R$=10.1 min. The KF of the starting mixture was 70 μg/ml.

A 0.1 ml sample of the reaction mixture was quenched into 0.1N HOAc solution (2–3 ml) and then diluted to 10 ml with CH$_3$CN in a volumetric flask. HPLC conditions [25 cm Zorbax® Phenyl column; CH$_3$CN:H$_2$O with 0.1% phosphoric acid: 75:25 gradient elution to 90:10 at 18 min, hold 90:10 until 22 min; flow=1.5 mL/min, UV detection at 210 nm.] Starting diols $t_R$=5.4, 5.8 min, intermediate Δ-4 eneone $t_R$=6.4 min, dieneone $t_R$=12.1 min.

The reaction was considered complete when the level of starting diol was <3 area % (8 hours). Once complete the batch was cooled to 15°–20° C. and quenched with 3N HCl (120 ml). The two phase mixture was stirred for 20 min, and then allowed to settle. The lower aqueous layer was removed and the organic layer was washed with 5% NaCl (120 ml). The batch was concentrated in vacuo to one half volume (40°–60° C. at 150 mm). The distillation removed excess 2-butanone from the batch. The level of 2-butanone in the final batch was <2% of the toluene (using G.C.) and the KF was 60 μg/ml.

The toluene solution was treated with conc. HCl (3.5 mL) at 25° C., under N$_2$. The reaction was assayed by HPLC until the intermediate tertiary alcohol was completely converted to dieneone (ca. 1 h). The solution was washed with D.I. water (60 mL) and saturated NaHCO$_3$ (60 ml). The pH of the bicarbonate wash was 8.5. (NOTE: The decomposition reaction will turn black if run for longer than 8 hours.) The resulting red solution (128 ml) contained 202 mg/ml of dienone.

Step 4:

Transfer Hydrogenation

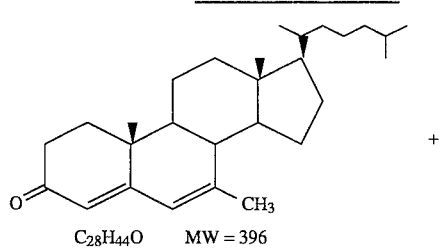

C$_{28}$H$_{44}$O   MW = 396

+

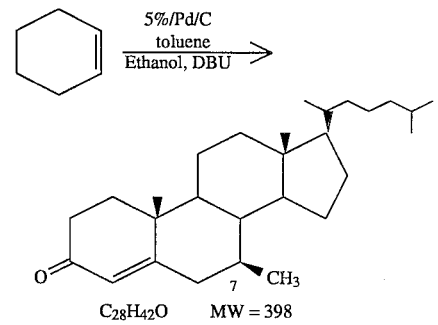

C$_{28}$H$_{42}$O   MW = 398

| Materials | Amt | MMole | MW |
|---|---|---|---|
| Dieneone (toluene solution) | 31.5 g | 79.5 | 396.7 |
| 5% Palladium on carbon (dry) | 4.5 g | | |
| Cyclohexene (d = 0.811) | 120 mL | 1.18 mole | 82.15 |
| 1,8 diazabicyclo[5.4.0]undec-7-ene (DBU) | 0.63 mL | 4.2 | 152.2 |
| Absolute ethanol | 495 mL | | |
| 3N HCl | 150 mL | | |
| half saturated NaHCO$_3$ | 100mL | | |
| Solka Flok | | | |
| Hexanes | 250 mL | | |
| t-butanol | 175 mL | | |

The toluene solution of the dieneone (150 ml at 214.6 mg/ml) was diluted with ethanol (120 mL) and cyclohexene (120 mL) and DBU (0.62 mL). To the mixture was added 5% palladium on carbon (9.0 g of 50% water wet). The mixture was degassed using vacuum/nitrogen purges (3×). The slurry was then heated to reflux (reflux temperature=72° C). The reaction was monitored by HPLC.

A 2 ml sample of the reaction mixture was filtered through Solka Floc. The filtrate (0.1 mL) was diluted to 10 ml with CH$_3$CN and analyzed by HPLC: 25 cm Zorbax® phenyl column; acetonitrile/water containing 0.1% phosphoric acid: gradient elution from 75:25 to 90:10 CH$_3$CN:water in 18 min, hold 90:10 until 22 min; flow=1.5 mL/min; UV detection at 200 nm.

Dienone $t_R$=12.1 min, Δ-4 enone $t_R$=13.2 min, Δ-5 enone $t_R$=14.1 min, over-reduced ketone $t_R$=14.4 min, ethyl enol ether $t_R$=20.9 min. The over-reduced ketone should be assayed at 192 nm.

The reaction was considered complete when the dieneone level was <2 A % and the Δ-5 enone level was 5% (about 10 hours). When the reaction was complete the mixture was cooled to ambient temperature. The palladium was removed by filtration through Solka Floc and the filter cake was washed with ethanol (150 mL).

The batch contained 51 mg/ml of enone. (NOTE: Prolonged reaction times should be avoided since over-reduction can occur. If the starting material has been consumed and the level of Δ-5 enone is >5% after 10 hours, then the palladium should be filtered, and the isomerization completed without catalyst present.)

The solution was concentrated under reduced pressure (75 mm) to a volume of approximately 150 mL. The batch was diluted with ethanol (225 mL) and re-concentrated to 150 mL.

The solvent switch to ethanol was considered complete when the toluene level was <2% of the ethanol by G.C., and there was no detectable cyclohexene. (NOTE: Removal of cyclohexene is important since it reacts in the subsequent oxidative cleavage step and unproductively consumes periodate.) A 0.1 ml sample was diluted to 1 mL with ethanol for the cyclohexene assay (and 1,1,1 trichloroethane for the toluene assay). G.C. conditions [HP-5 (25M×0.32 μm ID), using a heated block injector at 250° C., column temp at 35° C. isothermal, flow=0.5 ml/min] ethanol $t_R$=5.6 min, cyclohexene $t_R$=7.7 min, trichloroethane $t_R$=7.7 min, toluene $t_R$=10.2 min. The presence of cyclohexene is also detectable by $^1$H NMR (CDCl$_3$) of the solution: cyclohexene vinyl protons at δ=5.64 ppm, eneone vinyl proton at δ=5.69 ppm.

The concentrate was diluted with hexanes (250 mL) and 3N HCl (150 mL). The two phase mixture was warmed to 40° C. until enol ether hydrolysis was complete. The layers were separated and the organic layer was washed with half saturated sodium bicarbonate (100 mL). The hexane phase had a volume of 291 mL, contained less than 5% ethanol by volume and assayed for 92 mg/ml of enone.

The solution was concentrated to 100 ml under reduced pressure (100 mm/15° C.). The batch was diluted with t-butanol (175 ml) and m-concentrated to 100 ml (100 mm/40° C.). The batch contained 260 mg/ml of the desired 7β-methyl enone.

Step 5:

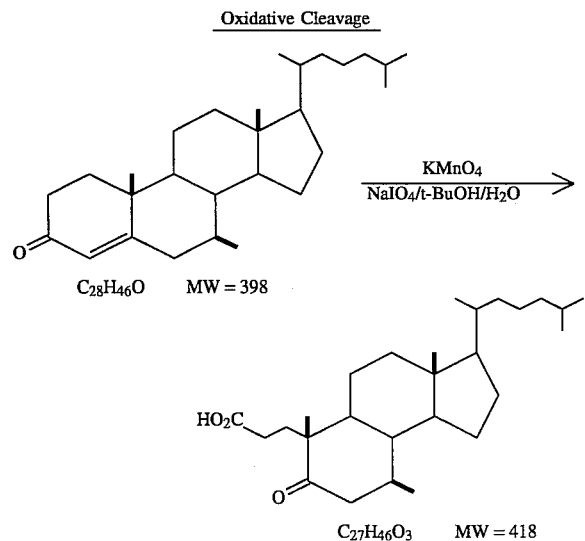

| Materials | Amt | Mol | MW |
|---|---|---|---|
| 7-β-Methylcholest-4-ene-3-one | 300 gm | 0.75 | 398 |
| t-Butanol (d = 0.786) | 6.6 L | | |
| Sodium carbonate | 159 gm | 1.5 | 106 |
| Sodium periodate | 1550 gm | 7.2 | 213.9 |
| Potassium permanganate | 11.1 gm | 0.07 | 158 |
| D.I. Water | 14.2 L | | |
| Diatomite | 50 gm | | |
| Ethyl acetate (d = 0.902) | 2.6 L | | |
| Heptane (d = 0.684) | 5.0 L | | |
| conc. Hydrochloric acid | 250 ml | | |
| 5% Aqueous NaCl | 2.5 L | | |
| Acetic acid (d = 1.049) | 9.0 L | | |

In a 5L roundbottom flask was charged D.I. water (4.93 L), sodium periodate (1.55 Kg) and potassium permanganate (11.1 gm). The slurry was stirred at 65° C. for 30 minutes to obtain complete solution.

To a solution of the enone (300 gm) in t-butanol (4.60 L) was added a solution of sodium carbonate (159 gm) in water (2.3 L). The two phase mixture was warmed to 65° C. The enone should be toluene, ethanol and cyclohexene free. (NOTE: Concentration of enone in organic layer is about 56 mgml$^{-1}$.) The sodium periodate solution was added to the enone solution over 3h with rapid stirring, maintaining the reaction temperature at 65° C. The slurry was aged at 65° C. for 2h. The periodate solution was added via a heated addition funnel.

Carbon dioxide gas was evolved during the reaction. A slow addition ensures controlled gas evolution. No exotherm was detected during addition. During the addition a purple/brown slurry was formed.

The reaction progress was monitored by HPLC. A 2 ml sample of the reaction mixture was cooled to 15° C. and filtered. The filtrate (0.1 mL) was diluted to 10 mL with water/CH$_3$CN (1:3). HPLC conditions [YMC Basic 25 cm×4.6 mm, CH$_3$CN, 0.01M H$_3$PO$_4$; 90:10 isocratic flow= 1.5 ml/min, UV detection at 200 nm]; enone $t_R$=11.5 min, seco-acid $t_R$=5.5 min.

The reaction was considered complete when the starting enone was <0.5 mg/mL. Water (3.0 L) was added and the slurry heated to reflux for 2 h to decompose any remaining KMnO$_4$ (color change from purple to brown) and to dissolve most of the solids precipitated on the vessel walls. The resultant slurry was cooled to 15° C. and filtered through dicalite (50 gm). The vessel and cake were washed with t-butanol/water (1:2, 6.0 L).

The filter cake was assayed for seco acid by dissolving 200–400 mg of cake with 50 mL water and 50 mL acetonitrile then filtering into the sample vial through diatomite to remove the small amount of orange manganese solids. The filtrates (pH=9.0–10.5) were extracted with heptane (5.0 L).

Ethyl acetate (2.6 L) was added to the aqueous mixture and the pH adjusted to 2.5±0.3 by the addition of conc. HCl (250 ml). The aqueous layer was removed.

The organic layer was washed with 5% aqueous brine (2×1.2 L). The ethyl acetate solution was concentrated (150 mm.Hg, 30° C.) to approx 10% volume. Acetic acid (7.4 L) was added and the residual ethyl acetate removed by concentration (100 mm. Hg, 60° C.) to <1% by volume (<0.5 area % by HPLC). The final volume was adjusted to 5.0 L by addition of acetic acid. Ethyl acetate removal was monitored by HPLC using the conditions above except the flow rate was 0.5 ml min$^{-1}$ and UV detection at 210 nm. Ethyl acetate $t_R$=7.4 min, acetic acid $t_R$=6.9 min. The assay yield was 275 gm. The acetic acid solution was used directly in the following step (ene-lactam formation).

Step 6:

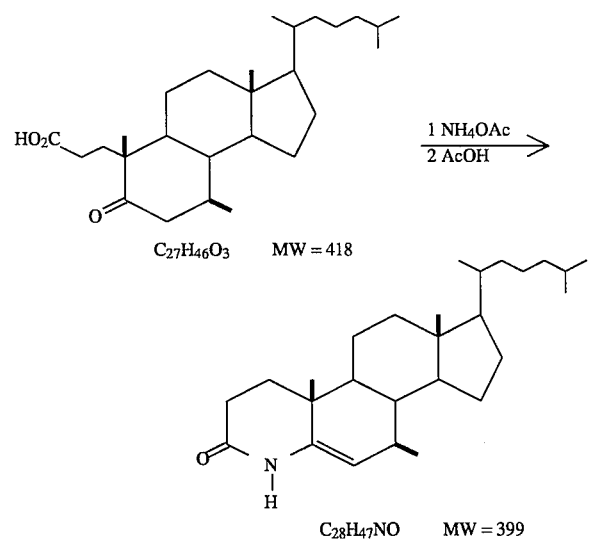

| Materials | Amt | Mole | MW |
| --- | --- | --- | --- |
| Seco-acid | 265 gm | 0.634 | 418 |
| Ammonium Acetate | 488 gm | 6.33 | 77.1 |
| 2,6-di-t-butyl-4-methylphenol (BHT) | 5.3 gm | 0.024 | 220 |
| D.I. Water | 565 ml | | |
| Acetic acid | 833 ml | | |

To a solution of seco-acid in acetic acid (265 gm in 5.3 L) obtained in the previous step was added BHT (5.3 gm) and ammonium acetate (488 gm) at 20° C. The slurry was warmed to a gentle reflux under a nitrogen atmosphere for 3 h. Complete solution was obtained at 30° C. The internal temperature was 120° C. at reflux. Color changed from yellow to dark red/brown. Use of reduced amounts of acetic acid results in oiling of the product at the crystallization stage.

The reaction progress was monitored by HPLC. HPLC conditions [SB Phenyl, $CH_3CN$, 0.01M $H_3PO_4$; isocratic 80:20 for 30 min, flow=1.5 ml/min, UV detection at 190/200 nm] Retention times: ene-lactam $t_R$=9.4 min, seco acid $t_R$=5.3 min. UV detection was at 190 nm for reaction progress and 200 nm for s.m. and product assay. The reaction was considered complete when <0.05 A% seco acid remained, about 3–4 hrs.

The reaction mixture was cooled to 60° C. and water (398 ml) added over 15 min. (NOTE: Addition of exactly 7.5% v/v water to the acetic acid solution is important.) The solution was allowed to cool to 50° C. and seeded with ene-lactam (1.0 gm). Crystallization occured at 50° C. The slurry obtained was aged at 50° C. for 1 h and then cooled to 0°–2° C. over 2 h.

The slurry was filtered and the light tan solid washed with 5:1 acetic acid/water (1.0 L).

Step 7:

NH-Enelactam Recrystallization

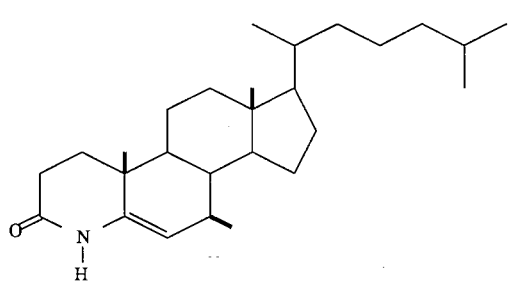

$C_{28}H_{47}NO$   MW = 399

| Materials | Amt | Mole | MW |
| --- | --- | --- | --- |
| Enelactam | 20 gm | 0.041 | 400 |
| D.I. Water | 17 ml | | |
| Acetic acid | 133 ml | | |
| BHT | 0.20 gm | 0.00091 | 220 |

To 20 gm at 83 wt% enelactam was added 100 mL acetic acid which contained 200 mg of BHT. The slurry was warmed to 60° C. under a nitrogen atmosphere to achieve dissolution, then cooled to 50° C. A charge of 10 mL water was then added. The mixture was then cooled to 5° C. over 1.5 hrs, aged for one hour and then the solid filtered off.

(NOTE: The solution at 50° C. should have started crystallizing before cooling to 5° C.) The solution Kf after BHT addition was about 0.2–0.4% w/w.

The mother liquor amounts were monitored by HPLC. HPLC conditions [SB Phenyl, $CH_3CN$, 0.01M $H_3PO_4$; isocratic 80:20 for 30 min, flow=1.5 ml/min, UV detection at 200 nm] Retention times: ene-lactam $t_R$=9.4 min. Sample 100 μl and dilute to 10 ml with acetonitrile.

The slurry was filtered and the light tan solid washed with 5:1 acetic acid/water (40 mL) at 5° C.

M.p. solvate is 112°–115° C. Pure m.p. is 175°–178° C., softens at 162° C.

Step 8:

N—H Enelactam Reduction

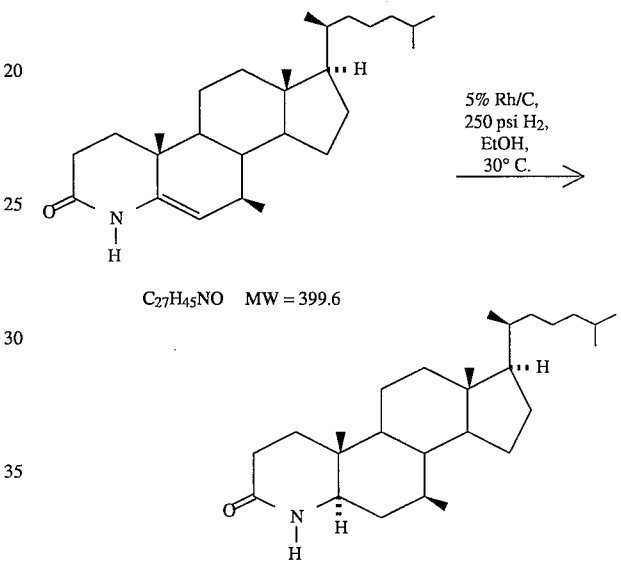

| Materials | Amount | Mol | MW |
| --- | --- | --- | --- |
| Enelactam | 1.02 gm | .0026 | 339.6 |
| Ethanol (punctillious) | 100 ml | | |
| BHT | 2 mg | | |
| 5% Rhodium on carbon | 200 mg | .097 mmol | 103 |

BHT (2 mg) was dissolved in degassed ethanol (100 ml) and the solution degassed with nitrogen purge. 5% Rhodium on carbon (200 mg) was added and the slurry degassed for a further 30 minutes with stirring. The resultant slurry placed under 250 psi of hydrogen in a stirred autoclave maintained at 30° C. The reaction progress was monitored by HPLC. HPLC conditions [Zorbax® Phenyl, MeOH, $H_2O$; 90:10 isocratic, flow=1.0 ml/min, UV detection at 210 nm]enelactam $t_R$=min, 5-α lactam $t_R$=12.4 min, 5-β lactam $t_R$=15.0 min.

After 24 hours the mixture was removed from the hydrogenator and the catalyst filtered off. Analysis of the solution by HPLC shows a 1:264 mixture of 5-β:5-α product. The solution was concentrated to give 0.92 grams of product as a white solid (m.p. 188°–190° C., 90% yield), NMR ($H^1CDCl_3$): 5.96(1H,brs), 3.05(1H,dd,J=12.3,3.5 hz), 2.38(2H,m), 2.0(1H,m), 1.75(3H,m), 1.60–0.7 (34H,m), 0.67(3H,s); ($C^{13}$ $CDCl_3$) 172.2, 59.6, 56.8, 55.3, 52.0, 44.1, 42.6, 40.1, 39.5, 37.9, 36.2, 35.7, 35.2, 35.1, 33.6, 28.7, 28.6, 28.0, 27.8, 23.9, 23.0, 22.8, 22.6, 21.8, 18.9, 12.5, 11.5.

If an N-alkyl compound of formula II is desired, lactam 8 may be N-alkylated as illustrated by Example 2 shown below.

EXAMPLE 2

Methylation of 7β-methyl-4-aza-5α-cholestan-3-one

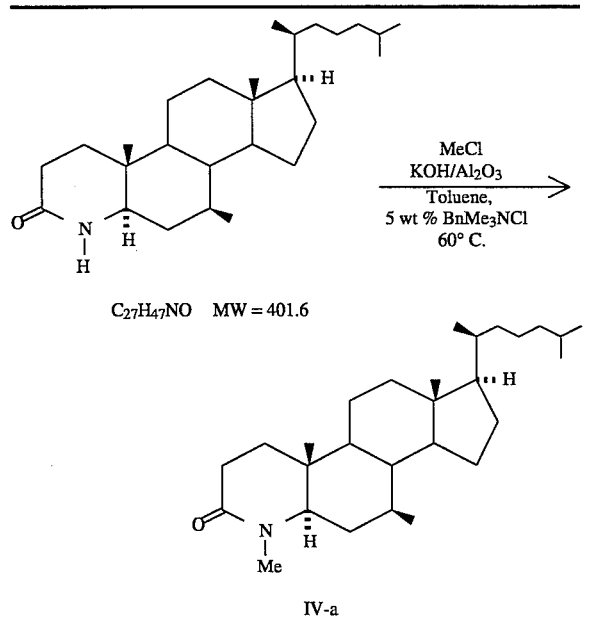

| Materials | Amount | Mol | MW |
|---|---|---|---|
| N—H Lactam | 3.0 Kg | 7.47 | 401.6 |
| Methyl chloride | 453 gm | 8.96 | 50.5 |
| KOH/Alumina[1:1] | 3.0 Kg | 22.8 | 56 |
| BnMe₃NCl | 150 gm | 0.81 | 185.7 |
| Toluene (d = 0.867) | 14.0 L | | |

A 5 gallon autoclave was charged with a slurry of lactam (3.0 Kg), BnMe$_3$NCl (150 gm) and potassium hydroxide on alumina (1:1, 3.0 Kg) in toluene (12 L) at room temperature. Methyl chloride (453 gm) was introduced at 20° C. with slow stirring. The slurry was heated to 65° C. with slow stirring and aged for 1 h. An exotherm at 52° C. of about 3° C. was noted as a spike on the temperature recorder.

The reaction progress was monitored by HPLC. HPLC conditions [Zorbax® SB phenyl, CH$_3$CN, 0.01M H$_3$PO$_4$; 90:10 isocratic, flow=1.5 ml/min, UV detection at 200 nm] lactam $t_R$=12.4 min, IV-a $t_R$=15.0 min. 25 μl Sample of toluene layer was diluted to 2 ml with acetonitrile. The reaction was monitored until complete conversion was obtained (>99.95%). The reaction was complete in <60 min at 60° C.

The reaction mixture was cooled to 20° C. and purged with nitrogen (4×) to remove any excess MeCl. The toluene solution was filtered through Solka Floc (100 gm) and the vessel and cake washed with toluene (2 L). The combined filtrates were concentrated at 100 mm. Hg and 20°–30° C. to a residual oil. The oil should be homogeneous in heptane (10 mlg-1) without any cloudiness.

The oil was assayed for toluene by G.C. oven temp 35° C. isothermal. The product (100 mg) was dissolved in methanol (0.5 ml) and 1 μl injected. Toluene $t_R$=4.4 min, methanol $t_R$=2.7 min.

The oil was kept under vacuum until the solvent level was <2%. The oil was poured into a glass tray and seeded with IV-a (1.25 gm) and allowed to stand in vacuo (20 mm. Hg) overnight.

The resulting solid was cut into blocks and broken up in a waring blender containing 2° C. water (10 L) to a particle size of <50 μm. The slurry was filtered, washed with water (5.0 L) and dried in a nitrogen stream overnight. Yield of product =3.0 Kg, 97%.

The process of the present invention can also be used to directly reduce an N-alkylated enelactam of formula I as illustrated by Example 3.

EXAMPLE 3

Preparation of 4,7β-dimethyl-4-aza-5-cholestan-3-one

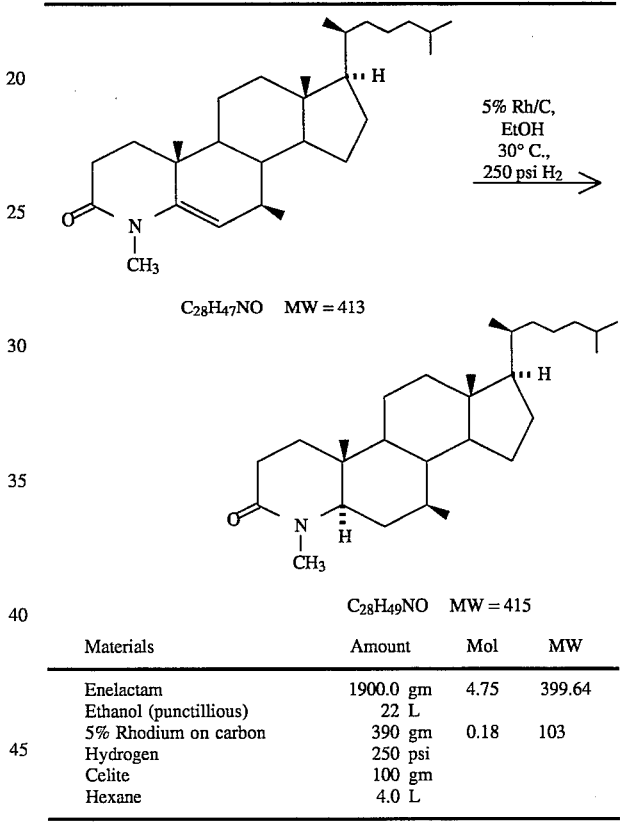

| Materials | Amount | Mol | MW |
|---|---|---|---|
| Enelactam | 1900.0 gm | 4.75 | 399.64 |
| Ethanol (punctillious) | 22 L | | |
| 5% Rhodium on carbon | 390 gm | 0.18 | 103 |
| Hydrogen | 250 psi | | |
| Celite | 100 gm | | |
| Hexane | 4.0 L | | |

Enelactam (1900.0 gm) was dissolved in ethanol (8.0 L) and the solution degassed with nitrogen purge for 18 h. 5% Rhodium on carbon (380 gm) was added and the slurry degassed for a further 30 minutes with stirring. The resultant slurry was charged to a 5 gallon stirred autoclave.

A further charge of degassed ethanol (4.0 L) was used to rinse the starting material and catalyst into the autoclave. The hydrogenation was performed at 30° C. and 250 psi hydrogen pressure for 18 h. Typically <4% ene-lactam remains after 18 h.

The reaction progress was monitored by HPLC, [YMC-basic, CH$_3$CN, 0.1M H$_3$PO$_4$; 1.5 ml/min, λ, =210 nm]. Retention times: Enelactam 16.1 min, trans-lactam 13.8 min, cis-lactam 13.1 min, 7-des methyl trans-lactam 12.4 min. Samples for HPLC analysis were removed without introducing oxygen into the system.

The hydrogenation mixture was filtered through celite (100 gm). Ethanol (8.0 L) was used to rinse the autoclave and wash the cake. The celite was washed with ethanol (2000 ml).

The combined colorless filtrate was concentrated to residue at 75 mm. Hexane (4.0 L) was added, concentrated to residue and assayed for product. Analysis of the solution by HPLC shows a 1:500 mixture of 5-β:5-α product. The assay yield was 1.86 Kg (98%). The crude product contained unreacted ene-lactam (1.8%), 7-des methyl trans-lactam (<0.1%) and cis-lactam (<0.2%). The hydrogenation also produced 0.07% overreduced product which lacks the lactam carbonyl oxygen.

The resulting oil was chromatographed on silica gel (17 Kg, 230–400 mesh) eluting with 1:3 v/v ethyl acetate: hexane (100 L) followed by 3:1 v/v ethyl acetate: hexane (140 L). The fractions containing the 5α/β products were combined and concentrated under vacuum. The resultant oil was seeded with 5α product (1.0 gm) and allowed to crystallize over 5 days. The resulting solid was ground in a morter and pestle to give 4,7β-dimethyl-4-aza-5α-cholestan-3-one (1.53 Kg) as a white, low melting crystalline solid, m.p. 58°–62° C., NMR ($H^1CDCl_3$): 3.02(1H, dd, J=12.7, 3.6), 2.92(3H, s), 2.43(2H, m), 2.01(1H, dt, J=12.3, 3.2), 1.92(1H, dt, J=12.7, 4.0), 1.89–1.70(3H,m), 1.58(1H, m), 1.52(1H,m), 1.41–0.96(17H, m), 1.05(3H, d, J=6.3), 0.92(3H, d, J=6.3), 0.87(3H, d, J=6.7), 0.86(3H, d, J=6.7), 0.84(3H, s), 0.81(1H, m), 0.68(3H, s), ($C^{13}CDCl_3$): 170.6, 64.7, 56.8, 55.2, 52.6, 44.0, 41.7, 40.1, 39.5, 36.1, 35.9, 35.8, 35.7, 33.1, 29.1, 28.6, 28.0, 27.7, 23.8, 23.2, 22.8, 22.5, 21.7, 18.8, 12.6, 12.4.

EXAMPLE 4

Preparation of 7β-methyl-4-aza-5β-cholestan-3-one

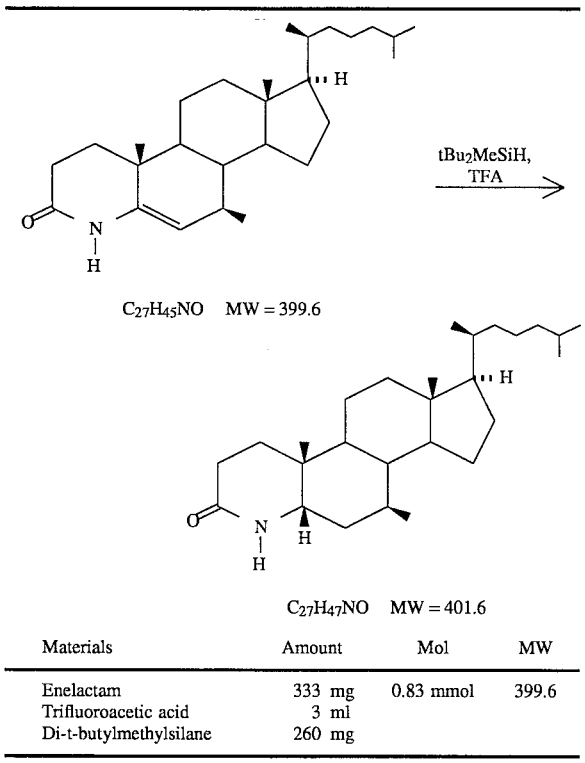

| Materials | Amount | Mol | MW |
|---|---|---|---|
| Enelactam | 333 mg | 0.83 mmol | 399.6 |
| Trifluoroacetic acid | 3 ml | | |
| Di-t-butylmethylsilane | 260 mg | | |

To 333 mg of enelactam (0.83 mmol) in 3 ml of trifluoroacetic acid was added 260 mg di-t-butylmethylsilane (1.64 mmol) and the mixture heated to reflux for about 2 hours until no enelactam remains. The mixture was cooled, concentrated to an oil, dissolved in hexane and washed with water twice.

Analysis of the mixture by HPLC showed a 90:1 ratio of 5-β:5-α product. Chromatography on silica using ethyl acetate gave 291 mg of product as a white solid (m.p. 90°–94° C., 87% yield).

As in preparation of the a-reduction product, the process of this invention can be used to produce 5β-reduction products of N-H enelactams which can be subsequently N-alkylated as in Example 2 or to directly reduce N-alkylated enelactams as in Example 3.

While the foregoing specification teaches the principles of the present invention, with examples provided for the purpose of illustration, it will be Understood that the practice of the invention encompasses all of the usual variations, adaptations, and modifications, as come within the scope of the following claims and its equivalents.

What is claimed is:

1. A process for the stereoselective reduction of a Δ-5 steroidal enelactam of the formula I, wherein R is selected from H and $C_{1-5}$ alkyl, and $R^1$ is $C_{1-10}$ alkyl;

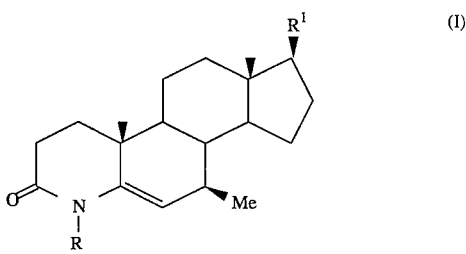

which comprises a treatment selected from:

a) dissolving said Δ-5 steroidal enelactam in a solvent in the presence of a rhodium-based catalyst and treating with $H_2$; and b) refluxing said Δ-5 steroidal enelactam in an ionizing medium in the presence of a trialkylsilane of the formula $(R^2)_3SiH$, wherein $R^2$ is selected from $C_{1-6}$ alkyl and phenyl.

2. The process of claim 1 for the stereoselective reduction of a Δ-5 steroidal enelactam of the formula I, wherein R is selected from H and methyl, and and $R^1$ is $C_{1-10}$ alkyl.

3. The process of claim 2 for the stereoselective reduction of a Δ-5 steroidal enelactam of the formula I, wherein $R^1$ is 6-methylhept-2-yl.

4. The process of claim 1 comprising treating the Δ-5 steroidal enelactam in the solvent with $H_2$ in the presence of a rhodium based catalyst to preferentially yield a 5α-azasteroid.

5. The process of claim 4 wherein the rhodium based catalyst is Rh/C (5%) and the solvent is a $C_{1-6}$ alcohol.

6. The process of claim 5 wherein the solvent is ethanol.

7. The process of claim 4 wherein the rhodium based catalyst is $Rh/Al_2O_3$ (5%) and the solvent is a $C_{1-4}$ alkanoic acid.

8. The process of claim 7 wherein the solvent is acetic acid.

9. The process of claim 4 wherein the quantity of catalyst is adjusted so that the amount of rhodium in the reaction mixture is between 5–100% of the weight of the steroidal enelactam starting material.

10. The process of claim 9 wherein the quantity of catalyst is adjusted so that the amount of rhodium in the reaction mixture is between 10–20% of the weight of the steroidal enelactam starting material.

11. The process of claim 10 wherein the amount of catalyst is adjusted so that the amount of rhodium in the reaction mixture is about 20% of the weight of the steroidal enelactam starting material.

12. The process of claim 4 where the reaction is run at a H$_2$ pressure between 40–250 psi.

13. The process of claim 12 where the H$_2$ pressure is about 40 psi.

14. The process of claim 4 where the reaction is run at a temperature of 20°–30° C.

15. The process of claim 14 where the reaction is run at room temperature.

16. The process of claim 1 in which the Δ-5 steroidal enelactam is refluxed in an ionizing medium with a trialkylsilane to preferentially yield the 5β-azasteroid.

17. The process of claim 16 where the ionizing medium is trifluoroacetic acid.

18. The process of claim 17 where the trialkylsilane is selected from di-t-butylmethylsilane and tri-t-butylsilane.

* * * * *